(12) United States Patent
Gagliardi et al.

(10) Patent No.: US 9,067,927 B2
(45) Date of Patent: Jun. 30, 2015

(54) (R)-NIFURATEL, ITS USE FOR THE TREATMENT OF INFECTIONS AND SYNTHESIS OF (R) AND (S)-NIFURATEL

(71) Applicant: POLICHEM SA, Luxembourg (LU)

(72) Inventors: Stefania Gagliardi, Vimercate (IT); Alessandra Consonni, Cassano Magnago (IT); Federico Mailland, Milan (IT); Anna Bulgheroni, Varese (IT)

(73) Assignee: POLICHEM SA, Luxembourg (LU)

( * ) Notice: Subject to any disclaimer, the term of this patent is extended or adjusted under 35 U.S.C. 154(b) by 0 days.

(21) Appl. No.: 14/607,464

(22) Filed: Jan. 28, 2015

(65) Prior Publication Data

US 2015/0148547 A1    May 28, 2015

Related U.S. Application Data

(63) Continuation of application No. 14/400,071, filed as application No. PCT/EP2013/055078 on Mar. 13, 2013.

(30) Foreign Application Priority Data

May 11, 2012   (EP) ..................................... 12167640

(51) Int. Cl.
*C07D 413/12*    (2006.01)
*A61K 31/422*    (2006.01)
*C07C 241/02*    (2006.01)
*C07D 263/26*    (2006.01)

(52) U.S. Cl.
CPC ............ *C07D 413/12* (2013.01); *C07C 241/02* (2013.01); *C07D 263/26* (2013.01); *A61K 31/422* (2013.01)

(58) Field of Classification Search
CPC ........................... C07D 413/12; A61K 31/422
USPC ......................................................... 548/230
See application file for complete search history.

(56) References Cited

FOREIGN PATENT DOCUMENTS

| CN | 101037435 | 9/2007 |
|---|---|---|
| EP | 2243482 | 10/2010 |
| GB | 969126 | 9/1964 |

OTHER PUBLICATIONS

International Preliminary Report on Patentability for PCT/EP2013/055078 of Jul. 25, 2014.
International Search Report with Written Opinion for PCT/EP2013/055078 of Apr. 8, 2013.

*Primary Examiner* — Robert Havlin
(74) *Attorney, Agent, or Firm* — Hueschen and Sage

(57) ABSTRACT

(R)-Nifuratel is disclosed together with its use as bactericide and bacteriostatic agent as well as the pharmaceutical compositions containing the same; (R)-nifuratel has been surprisingly found to possess a better antimicrobial profile than either nifuratel racemate or (S)-nifuratel. A new procedure for the synthesis of both (R)-Nifuratel and (S)-Nifuratel is also disclosed.

48 Claims, No Drawings

(R)-NIFURATEL, ITS USE FOR THE TREATMENT OF INFECTIONS AND SYNTHESIS OF (R) AND (S)-NIFURATEL

The present invention relates to (R)-Nifuratel, to the pharmaceutical compositions containing (R)-Nifuratel and to its use as bactericide and bacteriostatic agent. It also provides a new procedure for the synthesis of both (R)-Nifuratel and (S)-Nifuratel, whose chemical formulae are reported below.

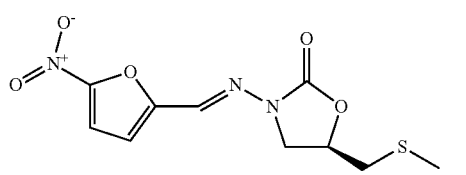

(R)-Nifuratel

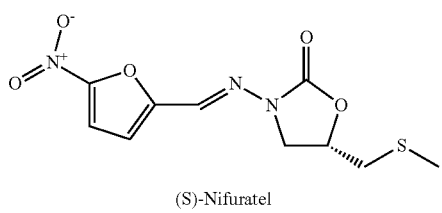

(S)-Nifuratel

BACKGROUND OF THE INVENTION

Nifuratel (CAS 4936-47-4) is a racemic nitrofurane derivative with a strong trichomonicidal activity and a broad antibacterial spectrum acting both on Gram-negative and Gram-positive organism. It is also active against *Chlamydia trachomatis* and *Mycoplasma* spp. Nifuratel has a very safe toxicological profile being non-toxic in acute tests in mice and rats and it is well tolerated after repeated oral and intravaginal administration. Since no teratogenic effects have been observed nifuratel is indicated also during pregnancy. This compound is currently used for the treatment of vulvo-vaginal infections and eradication of *Helicobacter pylori*. In contrast with other drugs used to treat the same diseases, no resistance phenomena, in course of nifuratel treatment, have been reported so far.

Nifuratel and the synthesis thereof are disclosed in GB969126. The Chinese patent application CN101037435A discloses the preparation of (S)-Nifuratel starting from enantiopure (S)-epichlorohydrine (CAS 67843-74-7) and using a chemical pathway similar to what already described for the synthesis of racemic Nifuratel. The same Chinese patent application discloses that (S)-Nifuratel has a better anti-inflammatory and anti-fungal activity than the racemic compound; no information is however given about the preparation of (R)-Nifuratel but that it has not been possible to isolate it by resolution of the racemic compound.

DESCRIPTION OF THE INVENTION

The present inventors have now surprisingly found a new synthetic reaction sequence that generates either pure (R)- or (S)-Nifuratel enantiomers [(R)- or (S)-5-(methylthiomethyl)-3-((5-nitrofuran-2-yl)methyleneamino)oxazolidin-2-one], depending on the stereochemistry of the reagent used in the first step. The present inventors have even more surprisingly found that (R)-nifuratel has a better antimicrobial profile than either nifuratel racemate or (S)-nifuratel.

An embodiment of the invention is therefore represented by (R)-nifuratel for use in the treatment of external genital infections, vaginal infections, urinary infections, gastrointestinal infections, respiratory infections either due to bacteria or protozoa.

Another embodiment of the invention is represented by a process for preparing (R)-Nifuratel or (S)-Nifuratel. Specifically the method of the invention includes the steps in Scheme 1 for the synthesis of the (R) enantiomer (Ia) and those in Scheme 2 for the synthesis of the (S) enantiomer (Ib).

Scheme 1

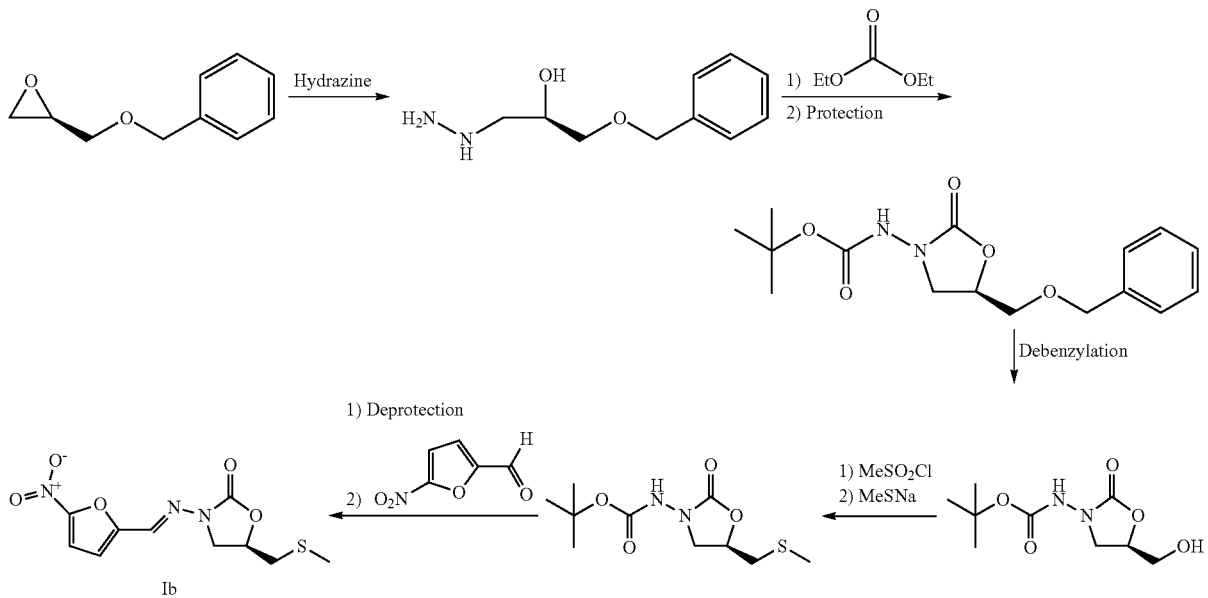

The first step, defined step (a), entails the reaction of commercially available (R)-2-(benzyloxymethyl)oxirane with hydrazine to obtain compound 1. This reaction is performed at suitable temperature, generally between 30 and 100° C., preferably at about 90° C., using an excess of hydrazine hydrate, typically from six to nine equivalents. The reaction is carried out in a polar solvent such as water or, preferably, in neat conditions (i.e. by performing the reaction in the reactant, without any additional solvent).

Conversion of compound 1 into compound 2, defined step (b), is preferably achieved by a first cyclisation of compound 1 to the 5-member ring oxazolidinone followed by protection of the free amino group. Cyclisation of compound 1 to the 5-member ring oxazolidinone is preferably achieved by reaction with a $C_1$-$C_4$-dialkyl carbonate, preferably diethyl carbonate, in presence of a catalytic amount of an alkaline or alkaline-earth metal $C_1$-$C_4$ alkoxide, preferably sodium methoxide or sodium ethoxide. The reaction is carried on neat or in a suitable solvent, preferably a polar organic solvent, such as methanol, THF or DMF, under conventional heating, generally at a temperature lower than 100° C., preferably from 60 to 90° C., depending on the solvent. Compound 2 is obtained after protection of the free amino group as a carbamate, preferably tert-butyl-carbamate. This chemical modification is achieved treating the compound with a $C_1$-$C_4$ alkyl chloroformate or $C_1$-$C_4$ alkyl carbonate, generally methyl-chloroformate, ethyl-chloroformate or di-tert-butyl dicarbonate, in a suitable solvent, preferably a polar organic solvent, such as THF or DMF at a suitable temperature, preferably lower than 100° C., preferably from 60 to 90° C., depending on the solvent.

Conversion of compound 2 into compound 3, namely the de-benzylation step (c), is preferably achieved by reaction at room temperature, preferably from 20 to 25° C., with $H_2$ at a suitable pressure, preferably from 15 to 45 psi, in presence of a suitable de-benzylating catalyst, such as palladium or platinum on carbon, preferably 10% palladium on carbon, in a suitable organic solvent, such as an alcohol, preferably a $C_1$-$C_4$ alcohol, more preferably methanol or ethanol, to give compound 3. The same reaction of debenzylation can be obtained under hydrogen transfer conditions, for example by heating compound 2 at a suitable temperature, preferably from 60 to 90° C., in presence of ammonium formate and a suitable de-benzylating catalyst, preferably a catalytic amount of 10% palladium on carbon in a suitable organic solvent, such as an alcohol, preferably a $C_1$-$C_4$ alcohol, more preferably methanol or ethanol.

Conversion of compound 3 into compound 4, namely step (d) is preferably achieved by first functionalizing the hydroxy group followed by reaction of the thus obtained-intermediate with an alkaline or alkaline-earth metal thiomethoxide. More in details, functionalization of the hydroxy group is obtained treating compound 3 with methanesulfonyl chloride, tosyl chloride, trifluoromethansulfonyl chloride or p-nitrobenzensulfonyl chloride, preferably methanesulfonyl chloride, in presence of a suitable base, such as triethylamine, in a suitable organic solvent, preferably an aprotic organic solvent such as methylene dichloride. This intermediate is then reacted with an alkaline or alkaline-earth metal thiomethoxide, preferably sodium thiomethoxide, in a suitable organic solvent, preferably a polar organic solvent such as DMF at a suitable temperature, generally room temperature, more preferably from 20 to 25° C., to give compound 4.

The conversion of compound 4 into (R)-Nifuratel, namely step (e), is preferably achieved by a first carbamate deprotection followed by reaction with 5-nitrofuran-2-carbaldehyde. Carbamate deprotection is preferably achieved through methods well known in the art, such as those disclosed in Green's Protective Groups in Organic Synthesis (Fourth Edition) Wiley-Interscience, herein incorporated by reference; preferably it is obtained by reacting a solution of compound 4 in a suitable organic solvent, preferably aprotic, such as THF with a solution of hydrogen chloride or trifluoro acetic acid, in a suitable organic aprotic solvent, preferably dioxane, at a suitable temperature, generally room temperature, more preferably from 20 to 25° C., for a suitable period of time, generally from 18 to 96 hours. The intermediate thus obtained, dissolved in a suitable polar organic solvent, generally an alcohol, preferably a $C_1$-$C_4$ alcohol, such as ethanol (or a mixture of such an alcohol with water, preferably a mixture ethanol/water), is reacted with the commercially available 5-nitrofuran-2-carbaldehyde dissolved in a suitable polar organic solvent, generally an alcohol, preferably a $C_1$-$C_4$ alcohol, such as ethanol, for a suitable period of time, typically from 15 to 60 min, at a suitable temperature, preferably room temperature, more preferably from 20 to 25° C., to obtain the desired (R)-Nifuratel (Ia).

For all the synthetic step described, after conventional work-up, the crude products may be purified, if necessary, by conventional purification methods, such as chromatography, trituration, crystallization or preparative HPLC.

The synthesis of (S)-Nifuratel (Ib) is obtained using the same reaction sequence but starting from commercially available (S)-2-(benzyloxymethyl)oxirane. The complete reaction sequence is reported in scheme 2.

Scheme 2

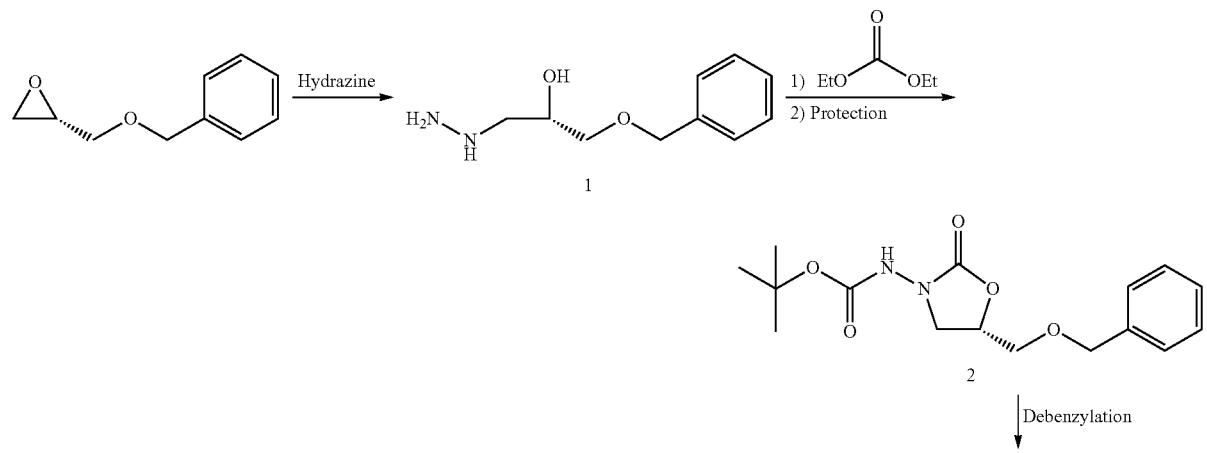

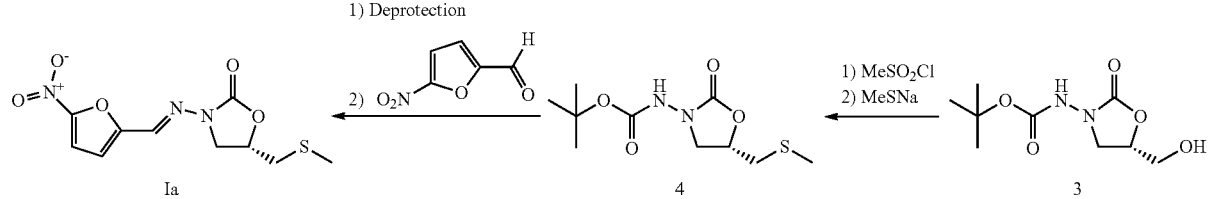

If necessary, enantiomeric excess of (S)- and (R)-Nifuratel could be further increase by crystallization in a suitable solvent such as, for example, acetonitrile/ethanol (1:1). The enantiomeric excess can be assessed using a chiral HPLC column such as Chiralcel OJ-RH 150×2.1 mm×5 µm. (Figure 1: Profile of (R)-Nifuratel (Ia) and Figure 2: Profile of (S)-Nifuratel (Ib))

(R)-Nifuratel can be formulated pharmaceutically according to known methods.

The compound of this invention can be administered in conventional manner, e.g. orally, intravenously, subcutaneously, transmucosally (including buccally, sublingually, transurethrally, and rectally), topically, transdermally, by inhalation, or using any other route of administration.

(R)-Nifuratel can be formulated pharmaceutically according to known methods. The pharmaceutical compositions can be chosen in function of the treatment. Said compositions are prepared by suitable mixing of their ingredients and are suitably adapted for oral or parenteral administration; they can be formulated as tablets, capsules, oral preparations, powders, granules, lozenges, regenerable powders, liquid injectable or infusible solutions, suspensions, emulsions or suppositories.

Tablets and capsules for oral administration are normally presented as unitary dosage form, and may contain conventional excipients such as binders, fillers, diluents, tabletting agents, lubricants, detergents, disintegrants, dyes, flavours and wetting agents. Tablets can be coated according to methods well known in the art.

Suitable fillers include cellulose, mannitol, lactose and further similar agents. Suitable disintegrants include starch, polyvinylpyrrolidone and starch derivatives such as starch sodium glycolate. Suitable lubricants include, e.g. magnesium stearate. Suitable wetting agents include sodium laurylsulphate.

Solid oral compositions can be prepared by conventional mixing, filling or compression. It is possible to repeat the mixing operations in order to disperse the active agent in compositions containing high amounts of fillers. These operations are conventional.

Liquid oral preparations can be formulated e.g. as aqueous or oily suspensions or solutions, emulsions, syrups or elixir, or can be presented as freezed dried product to be regenerated with water or with a suitable vehicle before use. Said liquid preparations can contain conventional additives such as suspending agents, e.g. sorbitol, syrup, methylcellulose, gelatine, hydroxyethylcellulose, carboxymethylcellulose, alluminium stearate gel or hydrogenated edible fats, emulsifying agents, e.g. lecithin, sorbitan monooleate, or acacia; non-aqueous vehicles (which may include edible oils), e.g. almond oil, fractionated coconut oil, oily esters such as glycerin esters, propylene glycol, or ethyl alcohol; preservatives, e.g. methyl or propyl p-hydroxybenzoate or sorbic acid and, if desired, conventional flavours and dyes.

Oral formulations include conventional sustained release forms, such as enteric coated tablets or granules.

For parenteral administration, it is possible to prepare fluid dosage units, containing the compound and a sterile vehicle. The compound, depending on the chosen vehicle and concentration, can be suspended or dissolved. Parenteral solutions are normally prepared by dissolving the compound in a vehicle, sterilising by filtration, filling suitable vials and sealing. Advantageously it is also possible to dissolve in the vehicle suitable adjuvants such as local anaesthetic, preservatives and buffering agents. In order to increase stability, the composition can be frozen after filling the vial and removing water under vacuum. Parenteral suspensions are prepared substantially in the same way, with the difference that the compound can be suspended rather than dissolved in the vehicle, and they can be sterilised by treatment with ethylene oxide before being suspended in the sterile vehicle. Advantageously, it is possible to include a surfactant or a wetting agent in the composition with the aim of easing the uniform distribution of the compound of the invention.

The compounds of the invention can be administered topically. Topical formulations may comprise, for example, an ointment, cream, gel, lotion, solution, paste or the like, and/or may be prepared so as to contain liposomes, micelles, and/or microspheres. Ointments, as is well known in the art of pharmaceutical formulation, are semisolid preparations that are typically based on petrolatum or other petroleum derivatives. Examples of ointments include leaginous ointment bases, for example, vegetable oils, fats obtained from animals, and semisolid hydrocarbons obtained from petroleum, emulsifiable ointment bases, for example, hydroxystearin sulfate, anhydrous lanolin and hydrophilic petrolatum, emulsion ointment bases, for example, cetyl alcohol, glyceryl monostearate, lanolin and stearic acid and water-soluble ointment bases prepared from polyethylene glycols of varying molecular weight. (See, e. g. Remington: The Science and Practice of Pharmacy, Twentieth Ed., Lippincott Williams & Willcins: Philadelphia, 2000) Creams, as also well known to those skilled in the art, are viscous liquids or semisolid emulsions, and contain an oil phase, an emulsifier and an aqueous phase. The oil phase is generally comprised of petrolatum and a fatty alcohol such as cetyl or stearyl alcohol. The aqueous phase usually contains a humectant. The emulsifier in a cream formulation is chosen among nonionic, anionic, cationic or amphoteric surfactants. Single-phase gels contain organic macromolecules distributed substantially uniformly throughout the carrier liquid, which is typically aqueous, but also, preferably, contain an alcohol and, optionally, an oil. Preferred gelling agents are crosslinked acrylic acid polymers (such as "carbomer" polymers, e. g., carboxypolyalkylenes that may be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. For the preparation of uniform gels, dispersing agents such as alcohol or glycerin can be added, or the gelling agent can be dispersed by trituration, mechanical mixing, and/or stirring.

The compounds of the invention may also be administered via transdermal release. Typical transdermal formulations include conventional aqueous and non-aqueous vectors, such as creams, oils, lotions or pastes or can be provided as membranes or medicated plasters. In an embodiment, a compound of the invention is dispersed in a pressure-sensitive plaster adhering to the skin. This formulation allows the compound to be spread from the plaster to the patient through the skin. In order to obtain a sustained drug release through the cutis, natural rubber and silicon can be used as pressure-sensitive adhesives.

As is common practice, the compositions are normally associated with written or printed instructions for use in the relevant treatments.

The dosage of (R)-Nifuratel is widely variable in function of the patient and his status, the degree of progress of the disease, the chosen way of administration, the chosen number of daily administrations, etc. As a reference they can be administered in a dosage interval comprised between 0.001 and 1000 mg/Kg/day.

EXPERIMENTAL SECTION

1. Chemical Synthesis

Unless otherwise indicated, all the starting reagents were found to be commercially available and were used without any prior purification. The compounds of the present invention can be readily prepared using conventional synthetic procedure. In these reactions, it is also possible to make use of variants which are themselves known to those of ordinary skill in this art, but are not mentioned in greater detail. Furthermore, other methods for preparing compounds of this invention will be readily apparent to the person of ordinary skill in the art in light of the following reaction schemes and examples. Unless otherwise indicated, all variables are as defined above.

Where reference is made to the use of an "analogous" procedure, as will be appreciated by those skilled in the art, such a procedure may involve minor variation, for example reaction temperature, reagent/solvent amount, reaction time, work-up conditions or chromatographic purification conditions.

Abbreviations used in the instant specification are summarized in Table 1.

TABLE 1

| UPLC (Ultra Performance Liquid Chromatography) | $R_t$ (retention time in minutes) |
| LC-MS (Liquid Chromatography Mass Spectrum) | ESI (Electro Spray Ionization) |
| | min (minutes) |
| | mmol (millimoles) |
| HPLC (High Performance Liquid Chromatography) | μl (microlitres) |
| h (hours) | HCl (hydrochloric acid) |
| μm (micrometers) | Pd/C (palladium on carbon) |
| TFA (trifluoroacetic acid) | Et$_2$O (diethyl ether) |
| psi (pound per square inch) | THF (tetrahydrofuran) |
| r.t. (room temperature) | CH$_3$CN (acetonitrile) |
| DCM (dichloromethane) | AcOEt (ethyl acetate) |
| MeOH (methanol) | Na$_2$SO$_4$ (Sodium sulfate) |
| DMSO (dimethylsulfoxide) | |
| DMF (dimethylformamide) | |

Except where otherwise indicated, all temperatures are expressed in ° C. (degrees centigrade) or K (Kelvin).

Proton Nuclear Magnetic Resonance ($^1$H-NMR) spectra were recorded on a Bruker 300 MHz. Chemical shifts are expressed in parts of million (ppm, δ units). Splitting patterns describe apparent multiplicities and are designated as s (singlet), d (doublet), t (triplet), q (quartet), quint (quintet), sxt (sextet), m (multiplet), br. s (broad singlet).

LC-MS were recorded under the following conditions:

Method A:

Acquity UPLC interfaced with a Mass Spectrometer Single Quadrupole ZQ (Waters): ESI positive mode. Column Acquity UPLC-BEH C18 (50×2.1 mm, 1.7 μm). Flow rate 0.5 mL/min, column at 40° C.

Mobile phases: A phase=H$_2$O/CH$_3$CN 95/5+0.1% TFA; B phase=H$_2$O/CH$_3$CN 5/95+0.1% TFA.

| Time (min) | % B | Flow |
| --- | --- | --- |
| 0.00 | 5.0 | 0.5 |
| 0.30 | 8.0 | 0.5 |
| 1.50 | 100.0 | 0.5 |
| 2.00 | 100.0 | 0.5 |
| 2.40 | 5.0 | 0.5 |

Method B.

UPLC with Sample Manager and 2996 PDA Detector (Waters) interfaced with a Mass Spectrometer Single Quadrupole ZQ (Waters). ZQ interface: ESI positive mode. Full scan from 102 to 900 amu. Capillary 3.2V, cone 25V, extractor 3V, RF 0.3V, source temperature 115° C., desolvation temperature 350° C., gas flow 800 l/h, cone 100 l/h. Column Acquity UPLC-BEH C18 (50×2.1 mm, 1.7 μm). Flow rate 0.6 mL/min, column at 40° C., injection 2 μl.

Mobile phases: A phase=H$_2$O/CH$_3$CN 95/5+0.1% TFA; B phase=H$_2$O/CH$_3$CN 5/95+0.1% TFA

| Time (min) | % B |
| --- | --- |
| 0.00 | 5.0 |
| 0.50 | 5.0 |
| 6.00 | 100.0 |
| 7.00 | 100.0 |
| 7.10 | 5.0 |
| 8.50 | 5.0 |

Method C.

Stationary phase: Chiralcel OJ-RH 150×2.1 mm×5 μm. Method: isocratic 70% A, 30% B. Flow rate: 0.3 mL/min Mobile phases: A phase=H$_2$O+0.1% acetic acid; B phase=CH$_3$CN Example 1

S-Nifuratel

1A.

(S)-3-amino-5-(benzyloxymethyl)oxazolidin-2-one (S)-2-(Benzyloxymethyl)oxirane (2.5 g, 15.23 mmol) was added dropwise to hydrazine mono-hydrate (5.44 g, 107 mmol), previously heated at 90° C. The mixture was refluxed for 30 min, under stirring. The excess of hydrazine hydrate was evaporated under vacuum (8 mbar), at 60° C., for 6 h and then at room temperature, under vigorous magnetic stirring, for 18 h. The obtained sticky colourless oil was dissolved in dry methanol (5 mL) and a solution of sodium methoxide (0.5M in MeOH, 4.57 mL, 2.28 mmol) and then diethyl carbonate (2.16 g, 18.27 mmol) were added dropwise. The mixture was refluxed for 4 h 30 min. Solvent was evaporated and the crude purified by flash silica-gel chromatography (DCM/MeOH=75:1) affording the title compound as a yellow oil that solidified (white solid) on standing (2.074 g, 9.33 mmol). Yield=61%.

$^1$H-NMR (DMSO-$d_6$, 303 K) δ: 7.22-7.44 (m, 5H); 4.56-4.66 (m, 1H); 4.53-4.56 (m, 2H); 4.52 (s, 2H); 3.62 (t, 1H); 3.61 (dd, 1H); 3.56 (dd, 1H); 3.34 (dd, 1H). LC-MS m/z (ESI+): 223.1 (MH$^+$), $R_t$=1.07 min (Method A).

1B. (S)-tert-Butyl 5-(benzyloxymethyl)-2-oxooxazolidin-3-ylcarbamate

To a solution of (S)-3-amino-5-(benzyloxymethyl)oxazolidin-2-one (2.06 g, 9.27 mmol) in dry THF (20 mL), di-tert-butyl dicarbonate (5.06 g, 23.17 mmol) was added and the mixture was stirred at 60° C., under nitrogen, for 6 h. Solvent was evaporated and AcOEt was added. The solution was washed with water, dried over Na$_2$SO$_4$ and the solvent evaporated under reduced pressure. The crude was purified by flash silica-gel chromatography (DCM/MeOH=200:1). Two products were isolated as white solid: the title compound (1.547 mg, 4.80 mmol) and (S)-ditert-butyl 5-(benzyloxymethyl)-2-oxooxazolidin-3-ylcarbamate (829 mg, 1.962 mmol). Yield=52% (Title compound).

$^1$H-NMR (DMSO-$d_6$, 303 K) δ: 9.31 (br. s, 1H); 7.27-7.42 (m, 5H); 4.75 (m, 1H); 4.56 (s, 2H); 3.53-3.80 (m, 3H); 3.44 (t, 1H); 1.41 (br. s, 9H).

LC-MS m/z (ESI$^+$): 345.1 (MNa$^+$), $R_t$=1.44 min (Method A).

(S)-ditert-butyl 5-(benzyloxymethyl)-2-oxooxazolidin-3-ylcarbamate $^1$H-NMR (DMSO-$d_6$, 303 K) δ: 7.24-7.43 (m, 5H); 4.77-4.94 (m, 1H); 4.57 (s, 2H); 3.78 (dd, 1H); 3.55-3.71 (m, 2H); 3.45-3.55 (m, 1H); 1.46 (s, 9H); 1.41 (s, 9H).

LC-MS m/z (ESI$^+$): 445.1 (MNa$^+$), $R_t$=1.73 min (Method A).

1C. (S)-tert-butyl 5-(hydroxymethyl)-2-oxooxazolidin-3-ylcarbamate

A solution of (S)-tert-butyl 5-(benzyloxymethyl)-2-oxooxazolidin-3-ylcarbamate (1.537 g, 4.77 mmol) in ethanol (25 mL), with 10% Pd/C (0.761 g, 0.715 mmol), was hydrogenated for 18 h at 40 psi. Conversion was about 40%. Catalyst was filtered away and replaced with fresh 10% Pd/C (0.254 g, 0.238 mmol); ammonium formate (0.752 g, 11.92 mmol) was added and the reaction was refluxed, under nitrogen, while stirring for 5 h. Conversion was complete. Catalyst was filtered away and the solvent evaporated. The residue was triturated with hot diisopropyl ether/MeOH (10:1) and left to precipitate on standing at r.t. The title compound was obtained as a white solid (802 mg, 3.45 mmol). Yield=72%.

$^1$H-NMR (DMSO-$d_6$, 303 K) δ: 9.28 (br. s, 1H); 5.15 (t, 1H); 4.34-4.65 (m, 1H); 3.64 (dd, 1H); 3.48-3.61 (m, 2H); 3.44 (t, 1H); 1.41 (s, 9H).

LC-MS m/z (ESI$^+$): 255.2 (MNa$^+$), $R_t$=0.94 min (Method A).

Analogously, 10% Pd/C (101 mg, 0.095 mmol) and ammonium formate (119 mg, 1.894 mmol) were added to a solution of (S)-ditert-butyl 5-(benzyloxymethyl)-2-oxooxazolidin-3-ylcarbamate (160 mg, 0.379 mmol) in MeOH (2 mL) and the mixture was refluxed, under nitrogen for 3 h. Additional ammonium formate (60 mg, 0.947 mmol) was added and the reaction was stirred at 70° C. After 15 h 30 min the conversion into the title compound was complete. The catalyst was filtered away and the filtrate evaporated. The sticky solid was triturated with diisopropyl ether/MeOH (2:1) and the title product was obtained as a white solid (71 mg, 0.306 mmol). Yield=81%.

$^1$H-NMR (DMSO-$d_6$, 303 K) δ: 9.27 (br. s, 1H); 5.15 (br. s, 1H); 4.40-4.74 (m, 1H); 3.64 (dd, 1H); 3.48-3.60 (m, 2H); 3.44 (t, 1H); 1.41 (s, 9H).

LC-MS m/z (ESI$^+$): 255.1 (MNa$^+$), $R_t$=0.93 min (Method A).

1 D. (S)-tert-butyl 5-(methylthiomethyl)-2-oxooxazolidin-3-ylcarbamate

To a turbid solution of (S)-tert-butyl 5-(hydroxymethyl)-2-oxooxazolidin-3-ylcarbamate (800 mg, 3.44 mmol) in DCM (5 mL), triethylamine (436 mg, 4.31 mmol) and methanesulfonyl chloride (493 mg, 4.31 mmol) were added and the reaction was stirred, at r.t., under nitrogen for 1 h 30 min. Conversion into the corresponding methanesulfonyl intermediate was complete. The solution was washed with cold citric acid (pH=4-5) and cold brine and the organic layer was separated and dried over Na$_2$SO$_4$. Evaporation of the solvent at 32° C. yielded a colourless foam (980 mg; yield=92%) that was dissolved in DMF (5 mL). Sodium methanethiolate (302 mg, 4.31 mmol) was added and the mixture stirred at 60° C. for 1 h. Conversion into the title product was complete. AcOEt was added and the solution was washed with cold citric acid (pH=3-4), then cold water and cold brine. The organic layer was dried over Na$_2$SO$_4$ and the solvent evaporated, leaving the title compound as a yellow sticky solid that was crystallized from diisopropyl ether into a white solid (404 mg, 1.539 mg). Yield=45%.

$^1$H-NMR (DMSO-$d_6$, 303 K) δ: 9.32 (br. s, 1H); 4.64-4.86 (m, 1H); 3.76 (t, 1H); 3.42 (t, 1H); 2.83 (dd, 1H); 2.77 (dd, 1H); 2.14 (s, 3H); 1.42 (s, 9H).

LC-MS m/z (ESI$^+$): 285.1 (MNa$^+$), $R_t$=1.27 min (Method A).

1E. (S)-3-amino-5-(methylthiomethyl)oxazolidin-2-one hydrochloride

To a solution of (S)-tert-butyl 5-(methylthiomethyl)-2-oxooxazolidin-3-ylcarbamate (374 mg, 1.426 mmol) in THF (2 mL), 4M HCl in dioxane (1.25 mL, 4.99 mmol) was added. The reaction was stirred at r.t. for 4 days and a white solid precipitated. The obtained product was filtered and triturated with hot diisopropyl ether affording the title compound (240 mg, 1.208 mmol). Yield=85%.

$^1$H-NMR (DMSO-$d_6$, 303 K) δ: 4.59-4.83 (m, 1H); 3.75 (t, 1H); 3.38 (dd, 1H); 2.80 (dd, 2H); 2.13 (s, 3H).

LC-MS m/z (ESI$^+$): 163.1 (MH$^+$), $R_t$=0.51 min (Method A).

1F. (S)-Nifuratel

To a suspension of (S)-3-amino-5-(methylthiomethyl)oxazolidin-2-one hydrochloride (230 mg, 1.158 mmol) in ethanol/water (1:1; 3 mL) a solution of 5-nitrofuran-2-carbaldehyde (163 mg, 1.158 mmol) in ethanol (2 mL) was added dropwise under stirring. The solution turned from colourless into dark yellow and the desired product precipitated as a yellow fine solid. After 30 min the product was filtered, triturated with diisopropyl ether and desiccated overnight under vacuum at room temperature. The title compound was obtained as yellow fine solid (303 mg, 1.062 mmol). Yield=92%. [α]$_D^{20}$=+128.2 (c 0.24, CHCl$_3$)

$^1$H-NMR (DMSO-d$_6$, 303 K) δ: 7.86 (s, 1H); 7.78 (d, 1H); 7.15 (d, 1H); 4.99 (dq, 1H); 4.10 (t, 1H); 3.69 (dd, 1H); 2.86-3.04 (m, 2H); 2.16 (s, 3H).

LC-MS m/z (ESI+): 286.1 (MH$^+$), R$_t$=1.25 min (Method A).

LC-MS m/z (ESI$^+$): 286.1 (MH$^+$), R$_t$=2.29 min (Method B).

LC-MS m/z (ESI$^+$): 286.0 (MH$^+$), R$_t$=6.33 min (Method C). ee 99.5%.

Example 2

(R)-Nifuratel 2A.
(R)-3-Amino-5-(benzyloxymethyl)oxazolidin-2-one (R)-2-(Benzyloxymethyl)oxirane (2.5 g, 15.23 mmol) was added dropwise to hydrazine mono-hydrate (4.67 g, 91 mmol), previously heated at 95° C., under vigorous stirring. The mixture was refluxed for 30 min. The excess of hydrazine hydrate was evaporated under vacuum for 3 h, at 53° C. and then at r.t., under vigorous magnetic stirring, for 18 h. A sticky colourless oil was obtained. The crude was dissolved in dry MeOH (5 mL) and a solution of sodium methoxide 0.5M in methanol (4.6 mL, 2.284 mmol), then diethyl carbonate (2.16 g, 18.27 mmol) were added dropwise. The mixture was refluxed for 6 h. The solvent was evaporated and the crude purified by flash silica-gel chromatography (DCM/MeOH=75:1) affording the title compound as a yellow oil that solidified on standing into a white solid (2.232 g, 10.04 mmol). Yield=66%.

$^1$H-NMR (DMSO-d$_6$, 303 K) δ: 7.25-7.42 (m, 5H); 4.56-4.66 (m, 1H); 4.55 (s, 2H); 4.51 (s, 2H); 3.63 (t, 1H); 3.61 (dd, 1H); 3.55 (dd, 1H); 3.34 (dd, 1H).

LC-MS m/z (ESI+): 223.2 (MH$^+$), R$_t$=1.08 min (Method A).

2B. (R)-tert-butyl 5-(benzyloxymethyl)-2-oxooxazolidin-3-ylcarbamate

To a solution of (R)-3-amino-5-(benzyloxymethyl)oxazolidin-2-one (2.069 g, 9.31 mmol) in dry THF (20 mL), di-tert-butyl dicarbonate (2.337 g, 10.71 mmol) was added and the mixture was stirred at 60° C., under nitrogen, for 12 h. A mixture of (R)-tert-butyl 5-(benzyloxymethyl)-2-oxooxazolidin-3-ylcarbamate (main product) and (R)-ditert-butyl 5-(benzyloxymethyl)-2-oxooxazolidin-3-ylcarbamate (minor product) was obtained. Solvent was evaporated and AcOEt was added. The organic layer, washed with 5% citric acid, sodium bicarbonate (aqueous saturated solution) and brine, was dried over Na$_2$SO$_4$ and then evaporated under reduced pressure. The crude was purified by flash silica-gel chromatography (DCM/MeOH=250:1 to 100:1). The title compound was obtained as a white solid (1.946 g, 6.04 mmol). Yield=65%.

$^1$H-NMR (DMSO-d$_6$, 303 K) δ: 9.31 (br. s, 1H); 7.23-7.50 (m, 5H); 4.63-4.96 (m, 1H); 4.56 (s, 2H); 3.52-3.87 (m, 3H); 3.44 (t, 1H); 1.41 (br. s, 9H).

LC-MS m/z (ESI+): 345.2 (MNa$^+$), R$_t$=1.45 min (Method A).

The minor product (R)-ditert-butyl-5-(benzyloxymethyl)-2-oxooxazolidin-3-ylcarbamate was recovered and characterized (283 mg, 0.670 mmol). Yield=7%.

$^1$H-NMR (DMSO-d$_6$, 303 K) δ: 7.22-7.46 (m, 5H); 4.77-4.95 (m, 1H); 4.57 (s, 2H); 3.78 (dd, 1H); 3.54-3.71 (m, 2H); 3.51 (t, 1H); 1.46 (s, 9H); 1.41 (s, 9H).

LC-MS m/z (ESI$^+$): 445.2 (MNa$^+$), R$_t$=1.73 min (Method A).

2C. (R)-tert-butyl 5-(hydroxymethyl)-2-oxooxazolidin-3-ylcarbamate

To a suspension of (R)-tert-butyl-5-(benzyloxymethyl)-2-oxooxazolidin-3-ylcarbamate (1.908 g, 5.92 mmol) and 10% Pd/C (315 mg, 0.296 mmol) in ethanol (25 mL), ammonium formate (933 mg, 14.80 mmol) was added and the reaction was refluxed, under nitrogen, while stirring for 3 h 30 min. The catalyst was filtered away and the solvent evaporated. The residue was triturated with diisopropyl ether:MeOH=10:1. The title compound was obtained as a white solid (852 mg, 3.67 mmol). Yield=62%.

$^1$H-NMR (DMSO-d$_6$, 303 K) δ: 9.27 (br. s, 1H); 5.15 (t, 1H); 4.26-4.68 (m, 1H); 3.64 (dd, 1H); 3.47-3.61 (m, 2H); 3.44 (t, 1H); 1.41 (s, 9H).

LC-MS m/z (ESI$^+$): 255.1 (MNa$^+$), R$_t$=0.93 min (Method A).

2D. (R)-tert-butyl 5-(methylthiomethyl)-2-oxooxazolidin-3-ylcarbamate

To a turbid solution of (R)-tert-butyl 5-(hydroxymethyl)-2-oxooxazolidin-3-ylcarbamate (840 mg, 3.62 mmol) in DCM (10 mL), triethylamine (458 mg, 4.52 mmol) and methanesulfonyl chloride (518 mg, 4.52 mmol) were added and the reaction was stirred, at r.t., under nitrogen, for 2 h 30 min. The solution was washed with: cold water (resulting pH=7-8), cold citric acid (resulting pH=4-5) and cold brine. The organic layer was dried over Na$_2$SO$_4$ and evaporated and the residue (beige foam) was triturated with diisopropyl ether, affording (S)-(3-(tert-butoxycarbonylamino)-2-oxooxazolidin-5-yl)methyl methanesulfonate (1.055 g, 3.40 mmol) as a white solid, that was dissolved in 7 mL of DMF. Sodium methanethiolate (317 mg, 4.52 mmol) was added to the solution and the mixture was stirred at 60° C. for 3 h. AcOEt was added and the solution was washed with cold water, cold citric acid (until pH=6) and cold brine. The organic layer was dried over Na$_2$SO$_4$ and evaporated to leave a yellow oil. The title compound was precipitated by crystallization from diisopropyl ether as a white solid, recovered by filtration on Buchner (429 mg, 1.635 mmol). Yield=45%.

$^1$H-NMR (DMSO-d$_6$, 303 K) δ: 9.32 (br. s, 1H); 4.75 (dq, 1H); 3.76 (t, 1H); 2.83 (dd, 1H); 2.77 (dd, 1H); 2.14 (s, 3H); 1.42 (s, 9H).

LC-MS m/z (ESI$^+$): 285.1 (MNa$^+$), R$_t$=1.24 min (Method A).

2E.
(R)-3-Amino-5-(methylthiomethyl)oxazolidin-2-one hydrochloride

To a solution of (R)-tert-butyl 5-(methylthiomethyl)-2-oxooxazolidin-3-ylcarbamate (429 mg, 1.63 mmol) in THF (3 mL), a solution of 4M HCl in dioxane (1.022 mL, 4.09 mmol) was added. The reaction was stirred at room temperature overnight under nitrogen. Conversion was complete. The title compound, precipitated as a white solid, was filtered, washed with diisopropyl ether and dried under vacuum, (260 mg, 1.31 mmol). Yield=80%.

$^1$H-NMR (DMSO-d$_6$, 303 K) & 4.67-4.84 (m, 1H); 3.81 (t, 1H); 3.43 (dd, 1H); 2.85 (dd, 1H); 2.79 (dd, 1H); 2.13 (s, 3H).

2F. (R)-Nifuratel

To a suspension of (R)-3-amino-5-(methylthiomethyl)oxazolidin-2-one hydrochloride (248 mg, 1.248 mmol) in ethanol/water (1:1; 3 mL) a solution of 5-nitrofuran-2-carbaldehyde (176 mg, 1.248 mmol) in ethanol (2.5 mL) was added dropwise under stirring. The solution turned from colourless into dark yellow and product precipitated as a yellow fine solid. After 20 min the product was filtered, triturated with diisopropyl ether and desiccated under vacuum overnight at room temperature and at 40° C. for 4 h. The title compound was obtained as a yellow powder (335 mg; 1.174 mmol). Yield=94%. $[\alpha]_D^{20}=-106.2$ (c 0.26, $CHCl_3$)

$^1$H-NMR (DMSO-$d_6$, 303 K) δ: 7.86 (s, 1H); 7.78 (d, 1H); 7.15 (d, 1H); 4.99 (dq, 1H); 4.10 (t, 1H); 3.69 (dd, 1H); 2.83-3.04 (m, 2H); 2.16 (s, 3H).

LC-MS m/z (ESI$^+$): 286.2 (MH$^+$), $R_t$=1.25 min (Method A).

LC-MS m/z (ESI+): 286.04 (MH$^+$), $R_t$=2.28 min (Method B).

LC-MS m/z (ESI$^+$): 285.97 (MH$^+$), $R_t$=5.80 min (Method C). ee≥98%.

Antimicrobial Activity

Organisms Used to Test the Activity of the Enantiomers

*Micrococcus pyogenes* (ATCC 11631), *Bacillus subtilis* (ATCC 11774), *Lactobacillus iners* (ATCC 55195), *Escherichia coli* (ATCC 11775), *Proteus mirabilis* (ATCC 14153), *Klebsiella pneumoniae* (ATCC 10031), *Shigella sonnei* (ATCC 11060), *Neisseria gonorrhoeae* (ATCC 19424), *Salmonella typhimurium* (ATCC 14028) *Salmonella paratyphi* B (ATCC 10719), *Helicobacter pylori* (ATCC 43504) and several strains of *Atopobium vaginae* and *Gardnerella vaginalis*.

Preparation and Conservation

Strains were prepared from freeze-dried pellets. An isolation of the suspensions (to test the strains purity) and a strains massive growth were made by streaking microbial suspensions on agar media. The bacterial colonies on agar plates were collected with 3-5 mL of specific liquid medium+15% glycerol and then the aliquots were frozen at −80° C.

Compounds Minimal Inhibitory Concentration (MIC) was determined through broth micro-dilution susceptibility testing with a method developed following the National Committee for Clinical Laboratory Standards (CLSI) M07-A8 and M11-A7 references. Assays were carried out in specific media (Table 3). The tests were performed either following the broth microdilution assay or the agar dilution assay. Compounds stock solutions were made at 12.8 mg/mL in DMSO 100%. A series of twofold dilutions were then prepared using the strain specific broth. Final concentrations were from 0.125 µg/mL to 64 µg/mL at 1% DMSO. MIC is defined as the lowest concentration of antibacterial agent which prevent any visible growth.

TABLE 2

|  | Growth media | Incubation |
| --- | --- | --- |
| GRAM POSITIVE | | |
| *Micrococcus pyogenes* | Nutrient agar | 37° C. 24 h |
|  | Nutrient broth | aerobic |
| *Bacillus subtilis* | Nutrient agar | 30° C. 48 h |
|  | Nutrient broth | aerobic |
| *Lactobacillus iners* | Columbia agar + 5% sheep blood | 35° C. 48-72 h |
|  | ATCC 1685 NYC III | microaerobic 5% $CO_2$ |
| *Atopobium vaginae* | Chocolate agar | 37° C. 72 h |
|  | BHI broth | anaerobic |
| GRAM NEGATIVE | | |
| *Escherichia coli* | Nutrient agar | 37° C. 24 h |
|  | Nutrient broth | aerobic |
| *Proteus mirabilis* | Nutrient agar | 37° C. 48 h |
|  | Nutrient broth | aerobic |
| *Klebsiella pneumoniae* | Nutrient agar | 37° C. 48 h |
|  | Nutrient broth | aerobic |
| *Shigella sonnei* | Nutrient agar | 37° C. 48 h |
|  | Nutrient broth | aerobic |
| *Helicobacter pylori* | Trypticase soy agar + 5% sheep blood | 37° C. 72 h |
|  | Brucella broth | microaerobic |
| *Salmonella typhimurium* | Nutrient agar | 37° C. 24 h |
|  | Nutrient broth | aerobic |
| *Salmonella paratyphi* B | Nutrient agar | 37° C. 24 h |
|  | Nutrient broth | aerobic |
| *Neisseria gonorrhoeae* | Columbia agar + 5% sheep blood | 37° C. 24-48 h |
|  | BHI broth | microaerobic 5% $CO_2$ |
| GRAM VARIABLE | | |
| *Gardnerella vaginalis* | Columbia agar + 5% sheep blood | 35° C. 48-72 h |
|  | Mueller Hinton + 5% sheep blood | anaerobic |

LC-MS m/z (ESI$^+$): 163.1 (MH$^+$), $R_t$=0.56 min (Method A).

Nifuratel enantiomers, prepared in the examples, were measured for their anti Gram positive and negative activity by the methods described above and compared with the MIC displayed by nifuratel racemate.

TABLE 3

MIC values obtained by the broth microdilution method

| | Nifuratel racemate | S-Nifuratel | R-nifuratel |
|---|---|---|---|
| Gram positive | | | |
| *Micrococcus pyogenes* ATCC 11631 | 1 | 1 | 2 |
| *Bacillus subtilis* | 0.5 | 1 | 0.25 |
| *Lactobacillus iners* ATCC 55195 | 16 | 32 | 16 |
| *Staphylococcus aureus* (MRSA) | 2 | 4 | 2 |
| Gram negative | | | |
| *Escherichia coli* ATCC 11775 | 1 | 2 | 1 |
| *Proteus mirabilis* ATCC 14153 | 8 | 8 | 8 |
| *Klebsiella pneumonia* ATCC 10031 | 2 | 4 | 2 |
| *Shigella sonnei* ATCC 11060 | 1 | 4 | 1 |
| *Neisseria gonorrhoeae* ATCC 19424 | 0.25 | 0.5 | 0.25 |
| *Salmonella typhimurium* ATCC 14028 | 4 | 8 | 2 |
| *Salmonella paratyphi B* ATCC 10719 | 2 | 4 | 1 |
| *Helicobacter pylori* ATCC 43504 | 0.125 | 0.25 | 0.125 |

TABLE 4

MIC values obtained by the agar dilution method

| | Nifuratel racemate | S-Nifuratel | R-nifuratel |
|---|---|---|---|
| *Atopobium vaginae* | | | |
| CCUG 48515 | 1 | 1 | 0.5 |
| CCUG 55226 | 1 | 1 | 1 |
| CCUG 42099 | 0.5 | 0.5 | 0.25 |
| CCUG 44156 | 0.5 | 0.25 | 0.25 |
| CCUG 39382 | 0.25 | 0.25 | 0.125 |
| CCUG 38953 | 0.125 | 0.25 | 0.25 |
| CCUG 43049 | 0.25 | 0.5 | 0.25 |
| CCUG 55227 | 0.25 | 0.5 | 0.25 |
| CCUG 44061 | 0.5 | 0.125 | 0.25 |
| *Gardnerella vaginalis* | | | |
| ATCC 14018 | 2 | 2 | 1 |
| C2 | 8 | 8 | 4 |
| D2 | 4 | 2 | 4 |
| E2 | 2 | 2 | 1 |
| G2 | 2 | 1 | 2 |
| H2 | 1 | 2 | 1 |
| J2 | 2 | 4 | 2 |
| K2 | 4 | 4 | 4 |

Both enantiomers retained a comparable activity with respect to nifuratel racemate. Overall, (R)-nifuratel showed a better antimicrobial profile when compared to either nifuratel racemate or (S)-nifuratel.

2. Rat Pharmacokinetic Profile of S- and R-Nifuratel

The pharmacokinetic profile of S- and R-nifuratel was assessed after intravenous administration (2 mg/kg) and oral gavage (15 mg/kg) in male rats.

Results obtained by the non compartmental analysis (Win-NonLin 5.1) of the pharmacokinetic data are reported as means in the table together with Nifuratel racemate data.

| IV (2 mg/Kg) | Nifuratel racemate | S-Nifuratel | R-Nifuratel |
|---|---|---|---|
| $T_{1/2}$ (min) | 24 | 8 | 11 |
| $T_{max}$ (min) | 2 | 2 | 2 |
| $C_{max}$ (ng/ml) | 555 | 1148 | 4194 |
| $T_{last}$ (min) | 120 | 53 | 75 |
| $C_{last}$ (ng/ml) | 5 | 5 | 43 |
| $AUC_{last}$ (min*ng/ml) | 7348 | 9969 | 44370 |
| $AUC_{inf}$ (min*ng/ml) | 7526 | 10022 | 44983 |
| Cl (ml/min/kg) | 267 | 203 | 49 |
| MRT (min) | 13 | 4 | 7 |
| $V_{ss}$ (l/kg) | 4.5 | 0.9 | 0.4 |
| XOS (15 mg/kg) | Nifuratel | S-Nifuratel | R-Nifuratel |
| $T_{1/2}$ (min) | 182 | na | 236 |
| $T_{max}$ (min) | 30 | 5 | 5 |
| $C_{max}$ (ng/ml) | 8 | 6 | 34 |
| $T_{last}$ (min) | 240 | 480 | 480 |
| $C_{last}$ (ng/ml) | 3 | 3 | 3 |
| $AUC_{last}$ (min*ng/ml) | 1218 | 1958 | 4008 |
| MRT (min) | 109 | na | 4944 |
| Mean Fpo (%) | 2.2 | 2.6 | 1.2 |

S- and R-nifuratel displayed a far better pharmacokinetic profile, following both 2 mg/kg intravenous administration and 15 mg/Kg oral administration, in comparison to nifuratel racemate, showing a slower clearance and higher Cmax and AUC. Overall, R-nifuratel showed the best pharmacokinetic profile following both oral and intravenous administration.

The invention claimed is:

1. A process for the manufacture of (S)-Nifuratel which comprises the following steps:

(a) reacting (S)-2-(benzyloxymethyl)oxirane with hydrazine to obtain compound 1;

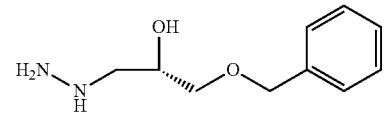 [SMILES: NNC[C@H](O)COCc1ccccc1]

(b) converting compound 1 into compound 2;

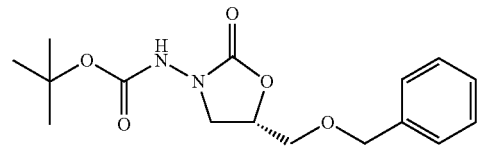 [SMILES: CC(C)(C)OC(=O)NN1C[C@@H](COCc2ccccc2)OC1=O]

(c) de-benzylating compound 2 to obtain compound 3;

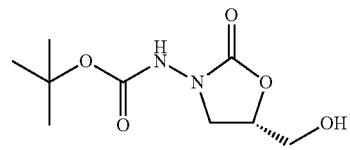 [SMILES: CC(C)(C)OC(=O)NN1C[C@@H](CO)OC1=O]

(d) converting compound 3 into compound 4;

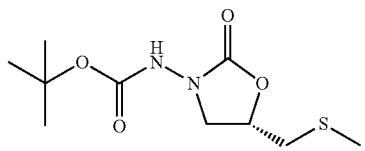 [SMILES: CSC[C@@H]1CN(NC(=O)OC(C)(C)C)C(=O)O1]

(e) converting compound 4 into (S)-Nifuratel.

2. The process according to claim 1, wherein step (a) is performed between 30 and 100° C.

3. The process according to claim 2, wherein step (a) is performed at about 90° C.

4. The process according to claim 1, wherein step (a) is performed in a polar solvent or under neat conditions.

5. The process according to claim 4, wherein step (a) is performed in water.

6. The process according to claim 1, wherein step (b) is performed by reacting compound 1 with a $C_1$-$C_4$-dialkyl carbonate in presence of a catalytic amount of an alkaline or alkaline-earth metal $C_1$-$C_4$ alkoxide, followed by protection of the free amino group as a carbamate.

7. The process according to claim 6, wherein the $C_1$-$C_4$-dialkyl carbonate is diethyl carbonate.

8. The process according to claim 6, wherein the alkaline or alkaline-earth metal $C_1$-$C_4$ alkoxide is sodium methoxide or sodium ethoxide.

9. The process according to claim 6, wherein the free amino group is protected as a tert-butyl-carbamate.

10. The process according to claim 7, wherein the reaction of compound 1 with diethyl carbonate is performed under neat conditions or in a polar organic solvent.

11. The process according to claim 10, wherein the polar organic solvent is methanol, THF or DMF.

12. The process according to claim 6, wherein protection of the free amino group is achieved by reaction with a $C_1$-$C_4$ alkyl chloroformate or a $C_1$-$C_4$ alkyl carbonate.

13. The process according to claim 12, wherein protection of the free amino group is achieved by reaction with methyl-chloroformate, ethyl-chloroformate or di-tert-butyl dicarbonate.

14. The process according to claim 6, wherein protection of the free amino group is performed in a polar organic solvent.

15. The process according to claim 14, wherein the polar organic solvent is THF or DMF.

16. The process according to claim 14, wherein protection of the free amino group is performed at a temperature lower than 100° C.

17. The process according to claim 16, wherein the temperature is from 60 to 90° C.

18. The process according to claim 1, wherein step (c) is performed at room temperature with $H_2$ at a suitable pressure in presence of a suitable de-benzylating catalyst in an alcohol.

19. The process according to claim 18, wherein the pressure is from 15 to 45 psi.

20. The process according to claim 18, wherein the de-benzylating catalyst is palladium or platinum on carbon.

21. The process according to claim 20, wherein the de-benzylating catalyst is 10% palladium on carbon.

22. The process according to claim 18, wherein the alcohol is a $C_1$-$C_4$ alcohol.

23. The process according to claim 22, wherein the alcohol is methanol or ethanol.

24. The process according to claim 1, wherein step (c) is performed under hydrogen transfer conditions.

25. The process according to claim 24, wherein compound 2 is heated at a suitable temperature in the presence of ammonium formate and a suitable de-benzylating catalyst in a suitable organic solvent.

26. The process according to claim 25, wherein the temperature is from 60 to 90° C.

27. The process according to claim 25, wherein the de-benzylating catalyst is 10% palladium on carbon.

28. The process according to claim 25, wherein the organic solvent is a $C_1$-$C_4$ alcohol.

29. The process according to claim 28, wherein the organic solvent is methanol or ethanol.

30. The process according to claim 1, wherein step (d) is achieved by first functionalizing the hydroxy group of compound 3, followed by reaction of the thus obtained-intermediate with an alkaline or alkaline-earth metal thiomethoxide.

31. The process according to claim 30, wherein functionalization of the hydroxy group is obtained by treating compound 3 with methanesulfonyl chloride, tosyl chloride, trifluoromethansulfonyl chloride or p-nitrobenzensulfonyl chloride in presence of a suitable base in a suitable organic solvent.

32. The process according to claim 31, wherein functionalization of the hydroxy group is obtained by treating compound 3 with methanesulfonyl chloride.

33. The process according to claim 31, wherein the base is triethylamine.

34. The process according to claim 31, wherein the organic solvent is an aprotic organic solvent.

35. The process according to claim 34, wherein the aprotic organic solvent is methylene dichloride.

36. The process according to claim 30, wherein the thus-obtained intermediate is reacted with an alkaline or alkaline-earth metal thiomethoxide in a polar organic solvent.

37. The process according to claim 36, wherein the alkaline or alkaline-earth metal thiomethoxide is sodium thiomethoxide.

38. The process according to claim 36, wherein the polar organic solvent is DMF.

39. The process according to claim 36, wherein the reaction is carried out at room temperature.

40. The process according to claim 1, wherein step (e) is achieved by a first compound 4 carbamate deprotection followed by reaction with 5-nitrofuran-2-carbaldehyde.

41. The process according to claim 40, wherein the carbamate deprotection is achieved by reacting a solution of compound 4 in an aprotic organic solvent with a solution of hydrogen chloride or trifluoro acetic acid in an organic aprotic solvent.

42. The process according to claim 41, wherein the aprotic organic solvent is THF.

43. The process according to claim 41, wherein the organic aprotic solvent is dioxane.

44. The process according to claim 41, wherein the reaction is carried out at room temperature.

45. The process according to claim 40, wherein the thus-obtained intermediate is reacted with 5-nitrofuran-2-carbaldehyde in a polar organic solvent.

46. The process according to claim 45, wherein the polar organic solvent is an alcohol.

47. The process according to claim 46, wherein the alcohol is a $C_1$-$C_4$ alcohol.

48. The process according to claim 47, wherein the alcohol is ethanol.

* * * * *